United States Patent [19]
Codignola

[11] Patent Number: 6,160,170
[45] Date of Patent: Dec. 12, 2000

[54] PROCESS FOR THE PRODUCTION OF AROMATIC ACIDS

[76] Inventor: Franco Codignola, Corso Lodi 59, 20139 Milano, Italy

[21] Appl. No.: 09/331,754

[22] PCT Filed: Jun. 14, 1997

[86] PCT No.: PCT/EP97/03154

§ 371 Date: Jun. 25, 1999

§ 102(e) Date: Jun. 25, 1999

[87] PCT Pub. No.: WO98/29378

PCT Pub. Date: Jul. 9, 1998

[30] Foreign Application Priority Data

Dec. 27, 1996 [IT] Italy ................................ MI96A2753

[51] Int. Cl.⁷ .................................................. C07C 51/215
[52] U.S. Cl. ............................................ 562/413; 562/414
[58] Field of Search .................................... 562/413, 414

[56] References Cited

U.S. PATENT DOCUMENTS 3,299,125  1/1967  Ichikawa et al. .
3,562,318  2/1971  Barone et al. ........................... 260/524
4,992,579  2/1991  Schammed .............................. 562/413

FOREIGN PATENT DOCUMENTS

| 0 026 507 | 4/1981 | European Pat. Off. . |
| 0 475 926 | 3/1992 | European Pat. Off. . |
| 0475926 | 3/1992 | European Pat. Off. . |
| 0 641 597 | 3/1995 | European Pat. Off. . |
| 831 902 | 4/1960 | United Kingdom . |
| 1041695 | 9/1966 | United Kingdom . |
| 1 063 964 | 4/1967 | United Kingdom . |

*Primary Examiner*—Paul J. Killos
*Attorney, Agent, or Firm*—Nixon & Vanderhye

[57] ABSTRACT

Process for producing mono- and poly-carboxylic aromatic acids by oxidation of the corresponding precursors with molecular oxygen and/or air in the presence of a catalytic complex formed by a combination of at least one metal selected from ruthenium, iridium, platinum and palladium, and/or at least one metal of Group VIIA, principally rhenium; and/or cerium, and B at least one metal belonging IVA of the periodic table of elements, principally zirconium and/or hafnium.

21 Claims, No Drawings

PROCESS FOR THE PRODUCTION OF AROMATIC ACIDS

The present invention relates to a new process for the production of mono- and poly-carboxylic aromatic acids by oxidation with molecular oxygen and/or air of aromatic compounds containing at least one oxidisable substituent group attached directly to the carbon atom of the corresponding aromatic ring.

The term "oxidisable substituent group" is to be understood as meaning any substituent in which a carbon atom is bonded directly to the aromatic ring and which, after oxidation, is converted into the COOH group, still bonded to the aromatic ring.

The methyl, methylene, hydroxymethyl, hydroxymethylene, ketone and aldehyde groups are considered to be among the more interesting oxidisable groups. The aromatic compounds used as starting materials in the present invention are therefore those which possess one or more of the mentioned oxidisable groups. In order better to illustrate the invention, there will be indicated hereinafter, purely by way of non-limiting example, some of the possible oxidations which can be carried out with the present invention:

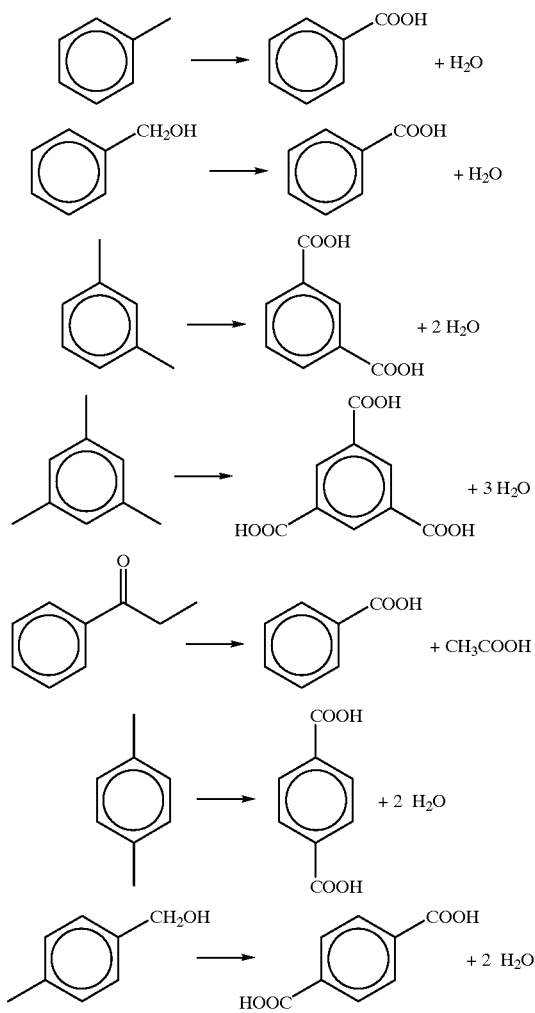

-continued

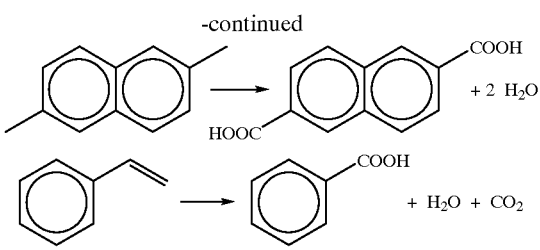

In particular, where there are two or more oxidisable groups, each of these groups has to be separated from the others by at least one carbon atom of the unsubstituted aromatic ring. With the process of the present invention it is thus not possible to oxidise o-xylene to phthalic acid, or 1,2-dimethylnaphthalene to 1,2-dinaphthoic acid.

According to the prior art, the above-mentioned oxidation processes are carried out with oxygen and/or air in the presence of a catalyst.

The catalysts known from the literature and used industrially in oxidation reactions of the type indicated above normally contain cobalt salts as the main active element, together with other metals, such as, for example, manganese.

These metals are usually used in the form of monocarboxylic aliphatic acid salts, preferably acetates, which are soluble in aqueous acetic acid, which is in fact the preferred solvent for aromatic compounds in this type of reaction.

However, both catalysts based only on the cobalt salt and bimetal catalysts have a disadvantage of not inconsiderable importance; they can oxidise only partially the oxidisable groups of the aromatic compounds in question.

In order to obtain complete oxidation, it is necessary to integrate the catalyst with suitable activators, which clearly involves per se an increase in the operating costs.

The activators of the oxidation catalysts can be of either inganic or organic character and perform the task of activating the oxidation reaction of the catalysts which can in turn be reduced during the oxidation of the aromatic compounds.

The use of activators of the first type, rather than the second, leads to two distinct oxidation processes.

The activator used in the first process is bromine in its various forms, that is to say: molecular bromine, hydrobromic acid, bromides, etc. The activating action of bromine, however, takes place at temperatures higher than 180° C., normally from 200 to 225° C., and at pressures of approximately from 20 to 25 bar. Given the high operating temperatures, the corresponding apparatus has to be constructed with materials having a particular thermal resistance, such as titanium or its alloys, which involves a further increase in costs.

The second process, however, uses acetaldehyde as the oxidation activator. In the course of the reaction, the acetaldehyde is oxidised to acetic acid with a yield of approximately 80%; the remaining acetaldehyde is, however, irretrievably burnt to $CO_2+H_2O$. This oxidation, in addition to involving a substantial waste of acetaldehyde, also has the disadvantage of substantially increasing the thermal charge of the reactor.

The conversion of acetaldehyde into acetic acid is also a rather negative economic phenomenon, given that the cost of acetaldehyde is higher than that of acetic acid and the increase in weight from acetaldehyde to acetic acid is not sufficient to cancel the difference in cost.

U.S. Pat. No. 5,112,592 describes the use of metals of groups IIIA and IVA of the periodic table of elements, especially zirconium and hafnium, as activators of catalysts, for increasing the kinetics of the oxidation reactions in which catalytic complexes based on cobalt and manganese are used in the presence of bromine as activator.

The catalytic activity of zirconium and hafnium derives:

from the ability of their ions to reach a coordination number higher than 6, which increases and maintains the ratio of the number of ions having higher valencies to those having lower valencies in multivalent catalytic metals.

from the fact that the ions of zirconium and hafnium have stable valencies which do not interfere with the oxido-reduction kinetics of the ions of multivalent metals.

from the fact that the presence of the ions of zirconium and/or hafnium reduces the formation of dimers of multivalent catalytic metals which are normally less active than monomers.

The aromatic mono- and poly-carboxylic acids obtained by the processes specified above must then be purified by hydrogenation in aqueous solutions at elevated temperatures and pressures so that they can be used directly in the polycondensation installations used for the production of polymers having the most varied industrial uses (fibres, bottles and various containers, polyester resins, etc.).

The catalytic metals used in the process for the purification of the various crude aromatic carboxylic acids are palladium and rhodium supported on carbon or other inorganic supports resistant to the high temperatures of the purification process.

The purification process in its turn has a further disadvantage associated basically with the concentrations of zirconium and hafnium. Zirconium and/or hafnium acetates, once they have entered the purification reactor, tend to hydrolyse, precipitating as insoluble polymer oxides on the hydrogenation catalyst, with the consequent inactivation of the latter. This result, as described in the already mentioned U.S. Pat. No. 5,112,592, can be avoided by limiting the concentration of the soluble salts of hafnium and zirconium in the initial reaction mixture to a value of not greater than 250 ppm, which inevitably limits the efficiency of the process.

The aim of the present invention is therefore to provide a new process for the production of mono- and poly-carboxylic aromatic acids for catalytic oxidation, which is free from all the disadvantages mentioned above.

A process has now surprisingly been found, and constitutes the subject-matter of the present invention, for the oxidation of aromatic compounds containing at least one oxidisable substituent group directly attached to the carbon atom of the corresponding aromatic ring, in which the aromatic compound is reacted with air and/or oxygen in the presence of a catalytic complex, characterised in that the catalytic complex is formed by a combination of:

A. at least one metal having a valency higher than 2 and belonging to group VIIIA of the periodic table of elements, preferably ruthenium, iridium, palladium, platinum; and/or at least one metal of group VIIA, preferably rhenium; and/or cerium; and B. at least one metal of group IVA of the periodic table of elements, preferably zirconium and/or hafnium.

It has surprisingly been found that the above-defined catalytic complex is capable of catalysing almost completely the oxidation, with molecular oxygen and/or air, of aromatic compounds containing at least one oxidisable substituent group, to give the corresponding aromatic acids without the necessity for the use of activators such as bromine or acetaldehyde, and without the necessity for the imposition of undue limitation on the concentrations of zirconium and/or hafnium.

The reaction for the oxidation of the above-defined aromatic compounds is carried out in liquid phase and with omogeneous catalysts, using an aqueous organic solvent, preferably aqueous acetic acid, as the solvent.

The metals used in the implementation of the present invention are preferably employed in the form of organic acid salts soluble in the reaction solvent, preferably acetates. Alternatively, it is possible to use the related precursor chemical compounds of those organic salts, such as, for example, hydroxides, oxides, carbonates, etc., such as, for example, ruthenium oxide, which are able to react with the solvent used, forming the respective salts soluble therein. Since aqueous acetic acid is the preferred solvent, the metals used in the reaction will generally be present in solution in the form of acetates.

The metals of point B can be used either individually or in pairs; it is, however, preferable, but not necessary, for the metals of point A to be used individually because there is a possibility that they will interfere with one another, disturbing the oxido-reduction reaction.

As already mentioned above, the process forming the subject-matter of the present invention is not efficient in the case of adjacent oxidisable groups; this phenomenon is attributable to the chelation effect exerted on the metal ions, of which the catalytic action is thus inhibited, by adjacent carboxylic groups which are formed in the initial stage of the oxidation reaction.

The solvent preferably used is aqueous acetic acid, generally in a concentration variable from 85 to 98% by weight, preferably from 95 to 98% by weight.

In view of the fact that the activity of the metals of paragraph B appears to decrease as the temperature of the reaction for the oxidation of the aromatic hydrocarbons increases, the present invention is carried out at temperatures of from 90° C. to 150° C., preferably from 105° C. to 115° C.

Thus, by operating at relatively moderate temperatures, at least relative to the 100–275° C. indicated in U.S. Pat. No. 5,112,592, and with an especially limited content of water in the reaction environment, it is possible to use concentrations of hafnium and/or zirconium salts higher than 250 ppm, the hydrolysis of the same preventing the consequent precipitation of the corresponding insoluble oxides.

The oxidising agent of the present invention is preferably air, which can optionally be enriched with oxygen.

The total reaction pressure can vary from atmospheric pressure to 20 bar, preferably from 2 to 5 bar.

The ratio of the metals of point A to the metals of point B can vary from 1:1 to 1:0.01, and is preferably 1:0.3.

It is also preferable for the content of the metal or metals of group IVA in the reaction mixture to be approximately from 0.05 to 1 gram atom per gram mole of the aromatic compounds to be oxidised to the corresponding carboxylic acids.

The following examples will better explain the features of the present invention without thereby limiting the field of application thereof

EXAMPLE 1

There are charged into a 6-litre autoclave equipped with a turbine agitator, an air inlet, an air outlet with a trap cooled to −15° C:

|  |  |
|---|---|
| Acetic acid 4% H$_2$O | 4,000 g |
| m-xylene | 980 g |
| Cerium acetate 1 + ½H$_2$O | 170 g |
| Zirconium acetate | 12 g |

The autoclave is heated to 95° C. and pressurised with air until a pressure of 4 bar is reached.

After approximately 1 hour, the absorption of oxygen starts. After 5 hours, the absorption of oxygen is practically zero. The conversion yield is approximately 72% while the theoretical yield, taking into account the m-xylene removed from the air and condensed in the trap at the outlet of the autoclave, of m-toluic acid and 3-carboxybenzaldehyde present in the mother liquors is greater than 92%.

It should also be borne in mind that the reduction period of 1 hour is of no importance in a plant with total recycling of the mother liquors, where the mixture entering the oxidation reactor is already in the active state.

EXAMPLE 2

The oxidation operation is carried out under the same conditions as in Example 1 except that the content of cerium acetate 1+½ H$_2$O and of zirconium acetate is doubled.

The conversion yield increases to 95.5% while the theoretical yield is 94.5%.

EXAMPLE 3

The procedure is as in Example 1, using p-xylene instead of m-xylene.

Conversion yield 82%, theoretical yield 94.5%.

EXAMPLE 4

The procedure is as in Example 2, using p-xylene instead of m-xylene.

Conversion yield 86.5%, theoretical yield 95%.

EXAMPLE 5

The procedure is as in Example 1, using instead of the cerium acetate 66 g of 100% ruthenium oxide in the hydrated form soluble in aqueous acetic acid.

The conversion yield is 87% while the theoretical yield is 95.5%.

EXAMPLE 6

The procedure is as in Example 5, using p-xylene instead of m-xylene.

Conversion yield 88%, theoretical yield 96%.

EXAMPLE 7

The procedure is as in Example 1, using 2,6-dimethylnaphthalene instead of m-xylene.

Conversion yield 70%, theoretical yield 93%.

EXAMPLE 8

The procedure is as in Example 2, using 2,6-dimethylnaphthalene instead of m-xylene.

Conversion yield 75%, theoretical yield 93%.

What is claimed is:

1. Process for the production of mono- and poly-carboxylic aromatic acids, which comprises oxidizing an aromatic compound containing at least one oxidizable substituent group attached directly to the carbon atom of the corresponding aromatic ring with molecular oxygen and/or air in the presence of a catalytic system in homogeneous liquid phase, wherein the catalytic system consists essentially of a combination of:

(A) a metal of group VIIIB of the periodic table of elements selected from the group consisting of ruthenium, iridium, platinum and palladium; and/or at least one metal of group VIIA of the periodic table of elements; and/or cerium; in the form of the corresponding organic acid salts soluble in the reaction solvent; and (B) at least one metal of group IVA of the periodic table of elements, in the form of the corresponding organic acid salts soluble in the reaction solvent.

2. Process according to claim 1, wherein the metal of group VIIA is rhenium.

3. Process according to claim 1, wherein the metal of group IVA is selected from zirconium and hafnium.

4. Process according to claim 1, wherein the solvent is aqueous acetic acid.

5. Process according to claim 4, wherein the aqueous acetic acid is used in a concentration of from 85 to 98% by weight.

6. Process according to claim 5, wherein the aqueous acetic acid is used in a concentration of from 95 to 98% by weight.

7. Process according to claim 1, wherein the oxidation reaction takes place at a temperature of from 90 to 150° C.

8. Process according to claim 7, wherein the oxidation reaction takes place at a temperature of from 105 to 115° C.

9. Process according to claim 1, wherein the oxidation reaction takes place at a pressure of from 0 to 20 bar.

10. Process according to claim 9, wherein the oxidation reaction takes place at a pressure of from 3 to 5 bar.

11. Process according to claim 1, wherein the ratio by weight of the metals of point A to the metals of point B is from 1:1 to 1:0.01.

12. Process according to claim 11, wherein the ratio by weight is 1:0.3.

13. Process according to claim 1, wherein the content in the reaction mixture of the at least one metal of group IVA is from 0.05 to 1 gram atom per gram mole of the aromatic compounds to be oxidised to the corresponding carboxylic acids.

14. Process according to claim 1, wherein the organic salts of the metals are introduced into the reaction mixture in the form of the corresponding precursor chemical compounds which can react with the solvent used, forming the respective salts soluble therein.

15. Process according to claim 14, wherein the precursor chemical compounds are selected from the corresponding hydroxides, oxides, carbonates.

16. Process according to claim 1, wherein the aromatic compound containing at least one oxidisable substituent group directly attached to the carbon atom of the corresponding aromatic ring is toluene.

17. Process according to claim 1, wherein the aromatic compound containing at least one oxidisable substituent group directly attached to the carbon atom of the corresponding aromatic ring is p-xylene.

18. Process according to claim 1, wherein the aromatic compound containing at least one oxidisable substituent group directly attached to the carbon atom of the corresponding aromatic ring is m-xylene.

19. Process according to claim 1, wherein the aromatic compound containing at least one oxidisable substituent group directly attached to the carbon atom of the corresponding aromatic ring is mesitylene.

20. Process according to claim 1, wherein the aromatic compound containing at least one oxidisable substituent group directly attached to the carbon atom of the corresponding aromatic ring is 2,6-dimethylnaphthalene.

21. Process for the production of a mono- or polycarboxylic aromatic acid, which comprises oxidizing an aromatic compound containing at least one oxidizable substituent group attached directly to the carbon atom of the corresponding aromatic ring with molecular oxygen and/or air in the presence of a catalytic system in homogeneous liquid phase in the absence of an activator, wherein the catalytic system contains a combination of:

(A) at least one metal having a valency higher than 2 and belonging to group VIIIA of the periodic table of elements; and/or at least one metal of group VIIA of the periodic table of elements; and/or cerium; in the form of the corresponding organic acid salts soluble in the reaction solvent; and (B) at least one metal of group IVA of the periodic table of elements, in the form of the corresponding organic acid salts soluble in the reaction solvent.

\* \* \* \* \*